US008828362B2

(12) United States Patent
Busch et al.

(10) Patent No.: US 8,828,362 B2
(45) Date of Patent: Sep. 9, 2014

(54) KITS, THEIR PRODUCTION AND METHOD FOR BRIGHTENING COATING OF TEETH

(75) Inventors: Susanne Busch, Neu Anspach (DE); Andreas Utterodt, Neu-Anspach (DE); Marcus Hoffmann, Usingen (DE); Christoph Maetzig, Alzenau (DE)

(73) Assignee: Heraeus Kulzer GmbH, Hanau (DE)

( * ) Notice: Subject to any disclaimer, the term of this patent is extended or adjusted under 35 U.S.C. 154(b) by 1293 days.

(21) Appl. No.: 11/942,064

(22) Filed: Nov. 19, 2007

(65) Prior Publication Data

US 2008/0241797 A1 Oct. 2, 2008

(30) Foreign Application Priority Data

Nov. 21, 2006 (DE) .......................... 10 2006 055 224

(51) Int. Cl.
| | | |
|---|---|---|
| A61Q 11/00 | (2006.01) | |
| A61K 6/00 | (2006.01) | |
| A61K 8/21 | (2006.01) | |
| A61K 8/02 | (2006.01) | |
| A61K 8/24 | (2006.01) | |

(52) U.S. Cl.
CPC . *A61Q 11/00* (2013.01); *A61K 8/21* (2013.01); *A61K 2800/88* (2013.01); *A61K 8/02* (2013.01); *A61K 2800/874* (2013.01); *A61K 8/24* (2013.01)
USPC .................. 424/49; 424/52; 424/57; 424/602

(58) Field of Classification Search
CPC ........................... A61K 2300/00; A61Q 11/00
USPC .................. 424/53, 52, 57, 49, 602
See application file for complete search history.

(56) References Cited

U.S. PATENT DOCUMENTS

| | | | |
|---|---|---|---|
| 4,083,955 A * | 4/1978 | Grabenstetter et al. ......... | 424/49 |
| 5,851,514 A | 12/1998 | Hassan et al. | |
| 6,102,050 A | 8/2000 | Marcon | |
| 6,303,104 B1 | 10/2001 | Winston et al. | |
| 6,419,905 B1 | 7/2002 | Hernandez | |
| 6,521,251 B2 | 2/2003 | Askill et al. | |
| 2005/0220724 A1 | 10/2005 | Busch et al. | |
| 2005/0281759 A1 | 12/2005 | Tung | |
| 2006/0110340 A1* | 5/2006 | Tung ............................... | 424/53 |
| 2006/0171904 A1 | 8/2006 | Vogel | |
| 2006/0292092 A1* | 12/2006 | Sharma et al. .................. | 424/53 |

FOREIGN PATENT DOCUMENTS

| | | |
|---|---|---|
| AT | 372272 | 9/1983 |
| DE | 10223157 | 10/2003 |
| EP | 0102200 | 3/1984 |
| EP | 1 645 263 A1 | 4/2006 |
| JP | 6024929 | 2/1994 |
| JP | 2000 051804 A | 2/2000 |
| JP | 2001172147 | 6/2001 |
| WO | 9810736 | 3/1998 |
| WO | 01 01930 A2 | 1/2001 |
| WO | 2005 027863 A1 | 3/2005 |
| WO | 2005092271 | 10/2005 |
| WO | 2006050966 | 5/2006 |

OTHER PUBLICATIONS

Ennever, J. et al., Influence of Alkaline pH on the Effectiveness of Sodium Fluoride Dentifrices, Journal of Dental Research, 1980, 59(4), pp. 658-661.*
Bitter et al; "The effect of four bleaching agents on the enamel surface; A scanning electron microscopic study": Dental Research; Quintessence International, vol. 24, No. 11, 1993; pp. 817-824.
Attin et al; "Susceptibility of enamel surface to demineralization after application of fluoridated carbamide peroxide gels"; Caries Research; 2003, 37; pp. 93-99.
Cavalli et al; "Effect of carbamide peroxide bleaching agents on tensile strength of human enamel"; Dental Materials; 2004; 20; pp. 733-739; Elsevier.
Nathanson, et al; "Bleaching vital teeth: a review and clinical study": Compend Contin Educ Dent., vol. VIII, No. 7; pp. 490-498.
Nathanson; "Vital tooth bleaching: Sensitivity and pulpal considerations"; JADA, vol. 128, Apr. 1997; pp. 41S-44S.

\* cited by examiner

*Primary Examiner* — Frederick Krass
*Assistant Examiner* — Tracy Liu
(74) *Attorney, Agent, or Firm* — Norris McLaughlin & Marcus, P.A.

(57) ABSTRACT

A method for brightening of teeth is described, using a kit with the components
A an alkaline, aqueous sodium fluoride solution, containing a gel former,
B a dried gel, present in film strips, containing
   B1 at least one gel former,
   B2 phosphate or hydrogen phosphate ions,
   B3 optionally at least one amino acid,
   B4 optionally fluoride,
   B5 optionally glycerol,
   B6 optionally a carboxylic acid or a buffer system for one of the pH values from 4 to 7.
C a dried gel, present in film strips, containing
   C1 at least one gel former,
   C2 calcium ions,
   C3 optionally glycerol,
as well as preparation of the kit.

12 Claims, 2 Drawing Sheets

KITS, THEIR PRODUCTION AND METHOD FOR BRIGHTENING COATING OF TEETH

The invention concerns kits for brightening coating of teeth, production of the kits and methods for brightening coating of teeth using them.

Glossy, radiating white teeth are considered healthy and possess high value in society. However, the products offered for tooth brightening do not promote actual health of the teeth. The teeth can become brittle and crack and their natural opalescence can be compromised. Modern nutrition promotes erosion of tooth substance, so that even without the occurrence of caries, the natural enamel layer becomes increasingly thinner, and the yellowish opaque color of the dentin shows through.

Bleaching systems that act by means of strong oxidizers are mostly used for brightening of teeth. Depending on the form of application, the concentrations lie between 10-35% peroxide. In particular, concentrated hydrogen peroxide solutions or carbamide peroxide are used. The action mechanism is based on oxidative decoloration of incorporated organic colorants. They have an aggressive effect on the oral mucosa, so the contact must absolutely be avoided. However, strong oxidizers also degrade structure-relevant proteins in the enamel. The content of natural macromolecules in dental enamel depends on the degree of maturation and is about 1-2 wt. % in adults. Proteins are preferably found on the surface of enamel prismatic units, but can also be integrated in the crystal structure. Composite systems of an inorganic mineral and organic components (preferably proteins and polysaccharides) are characteristics of biomineralization. The specific interaction leads to increased rupture strength. If the organic components are chemically removed, embrittlement must be reckoned with. Accessibility for contaminants, at least in the first days after treatment, is also increased during oxidative tooth brightening, and the sensitivity to pain is sometimes strongly increased. A fine pore system presumably becomes passable by oxidation of the biological matrix. Because of this, pain stimuli can be conducted more readily to the tooth nerve and undesired foreign substances can diffuse in better. Many bleaching systems function at low pH values, which can also lead to demineralization and entail additional weakening for the tooth. Topographic investigations on bleached human teeth show a detectable increase in natural porosity (cf. Bitter N. C. and Sanders J., L.: The effect of four bleaching agents on the enamel surface: A scanning electron microscopic study. *Quintessence Int* 1993, 24: 817-24). In addition, increased sensitivity to acid attack results. Although the hardness of the tooth shows no measurable reduction after the bleaching procedure, studies on bleached teeth demonstrate a distinct reduction in microhardness and intensified dissolution phenomena after simulated demineralization-remineralization cycles. The effect is somewhat reduced by providing fluoride, but weakening is not eliminated (cf. Attin T., Kocabiyik M., Buchalla W., Hanning C., Becker K.: *Susceptibility of Enamel Surfaces to Demineralization after Application of Fluoridated Carbamide Peroxide Gels*, Caries Res 2003: 37: 93-99). Another study demonstrates that the tensile strength and rupture strength of enamel diminishes by up to 30% after exposure to bleaching solutions (see: Cavalli, V. et al.: *Effect of carbamide peroxide bleaching agents on tensile strength of human enamel*. Dental Materials (2004) 20, 733-9). A pain study demonstrates that after treatment with 35% hydrogen peroxide solution, ⅔ of the patients reported moderate to severe pain, which lasted up to 48 hours after treatment (see Nathanson D., Parra C.: *Bleaching vital teeth: A review and clinical study*. Compend. Contin. Educ. Dent. 1987; 8(7): 490-7). The studies provide no clear indications of irreversible pulp damage, but in animal experiments, cases of massive inflammation, dentin resorption up to death of the pulp occurred during bleaching of vital dog teeth (see: Nathanson D.: *Vital tooth bleaching: Sensitivity and Pulpal considerations*, JADA, 128 (April 1997) 41-4). A prerequisite for conventional bleaching procedures, in each case, are healthy teeth. If hypersensitive teeth, exposed tooth necks or caries are present, bleaching can irreversibly damage the tooth nerve. It is also conceivable that damage from repeated bleaching can accumulate in healthy teeth.

Some forms of administration that are prescribed as suitable for stimulating mineralization of apatite on the tooth surface are known. U.S. Pat. No. 6,521,251 describes a composition that contains calcium phosphates, in addition to carbamide peroxide, whose solubility is somewhat better than that of apatite, like mono-, di- or tricalcium phosphate. However, all these calcium phosphates are only slightly water-soluble and, for this reason, more of an abrasive than a remineralizing effect is expected of them. U.S. Pat. No. 5,851,514 actually describes, among other things, the addition of dicalcium phosphate as an abrasive.

U.S. Pat. No. 6,419,905 mentions the addition of potassium salts (for example, phosphates) and fluoride to peroxide. Fluoride is suitable for bonding calcium and phosphate ions from saliva, so that fluorapatite (FAP) precipitates. If additional ions are not added, formation of $CaF_2$ is also observed. The calcium fluoride particles can be stored in the plaque and release fluoride over a longer period, since they are somewhat more soluble than apatite. However, all teeth are freed of plaque by intensive cleaning before professional bleaching. JP 20000051804 describes parallel use of concentrated phosphoric acid, concentrated $H_2O_2$ and fluorapatite powder. A problem appears here with the use of concentrated phosphoric acid, which can noticeably dissolve healthy dental enamel. In addition, the bleaching solution has a strong etching effect and must not come in contact with the gums, which, however, applies, to a somewhat lesser degree, for all tooth brighteners that have an oxidative effect. In addition, repeated application does not lead to an increase in the remineralization layer. It is suspected that the dental enamel dissolved here, at best, is reprecipitated. An acid-free application is described in US 20050281759. Calcium peroxophosphate is proposed as essential ingredient. This idea has the advantage that a single substance is supposed to have a brightening and remineralizing effect, since release of calcium and phosphate ions is triggered parallel with oxidation. It is not clear whether the salts can contribute to noticeable buildup over the relatively short exposure time. U.S. Pat. No. 6,303,104 describes a two-component system, free of oxidizer, from soluble calcium and phosphate salts, which is also supposed to have a brightening effect. Brightening is supposed to be produced by the additional sodium gluconate, which complexes coloring metal ions (for example, iron) from dental enamel. During mixing of the components, precipitation of the poorly soluble calcium phosphates must immediately be reckoned with and it cannot be recognized why pronounced mineralization should occur, especially since the product is a toothpaste that remains in contact with the tooth surfaces only a few minutes. The decoloring effect is also reduced to complexable metal ions and presumably will only exhibit an effect in the outermost enamel layers. U.S. Pat. No. 6,102,050 describes a dental floss with titanium dioxide particles that is attributed to a brightening, remineralizing and desensitizing effect on the interproximal surfaces. Here, titanium dioxide microparticles with a size of 0.1-1.5 µm are supposed to act both as a mild abrasive and are absorbed by the enamel, which is connected with a brightening effect. Presumably, the particles, at best, can be mechanically incorporated in appropriate cavities, which does not promise a stable effect and, at best, can have a temporary effect.

The aforementioned prior art does not consider that biominerals only achieve their high structural organization and stability, if they are formed in the presence of special biomolecules that dictate the micro- and macrostructure. WO 2005/027863 describes a dental hygiene agent, which is supposed to have a cleaning, remineralizing, desensitizing and brightening effect. A nanoscale apatite-gelatin-composite is mentioned as an active component for remineralization and brightening, which is precipitated in the presence of an aqueous gelatin solution and therefore has incorporated polypeptides. It is conceded to this material that it forms a protective film of dentin-like structure on the tooth surface by so-called "neomineralization," which causes surface smoothing and can close off open dentin tubuli. The fact that a toothpaste with a content of preferably only 0.01-2 wt. % of the so-called "nanite" (WO 01/01930) has such an effect during action of the active substances only for a few minutes is considered astonishing. A pronounced mineral deposition appears unlikely. In addition, discrete nanoscale particles are colorless, so that incorporation of nanite, especially in the layers in the submicrometer range, should not lead to a color change. Mineral deposition on the enamel is not described. Anyway, it is questionable whether and how the ordered structure of the nanoparticles could be transferred to the microscopic order of the prism structure in the enamel. A continuous growth of film thickness during longer application of the care agent is also not expected. The porous, not well ordered structure of dentin is also not capable of protecting teeth from corrosive attack. The protective film, with a dentin-like structure, therefore does not appear to be suitable for offering permanent protection.

The possibility of a continuously growing FAP-layer with an enamel- or dentin-like structure is offered by the technique described in US 20005220724 and DE 1020040545847. Water-soluble phosphate and fluoride salts are incorporated in buffered gel A, calcium ions in gel B. Optionally separated by an ion-free protective layer, the gelatin gels, solid at physiological temperature, are applied in succession to the tooth surfaces during heating. Depending on the exchange cycles of the gels, an increase in layer thickness can be observed. The growth rates amount to a maximum of 0.5-5 µm/day. The biological structures of the tooth material are formed individually by fluorapatite, but cavities through open dentin tubuli are closed after a few exchange cycles. With respect to human application, it turns out to be unfavorable that the gels must be heated before application. By application of the second and third gel layer, underlying already applied gel layers can be reliquefied and intermingle undesirably with the overlying layers. In particular, smaller forms of administration quickly dry up on exposure to air and liquefaction by heating is then no longer possible without a problem. The method permits application of precisely defined amounts of gel to the tooth only with difficulty. In addition, the three gel layers, up to 6 mm thick, spread strongly, which leads to problems in protective systems, like braces or bandages, since space must be created here for large gel reservoirs.

The invention concerns a method for deliberate coating of teeth with fluorapatite as a tooth-compatible alternative to the previously known oxidative bleaching procedures.

According to the invention, a kit is furnished for brightening of teeth, containing A an alkaline, aqueous sodium fluoride solution, containing a gel former, B a dried gel, present in film strips, containing
   B1 at least one gel former,
   B2 phosphate or hydrogen phosphate ions,
   B3 optionally at least one amino acid,
   B4 optionally fluoride,
   B5 optionally glycerol,
   B6 optionally a carboxylic acid or a buffer system for one of the pH values from 4 to 7,
C a dried gel, present in film strips, containing
   C1 at least one gel former,
   C2 calcium ions,
   C3 optionally glycerol.

BRIEF DESCRIPTION OF THE DRAWINGS

The invention will now be described in greater detail with reference to the drawings, wherein.

Figure 1A:
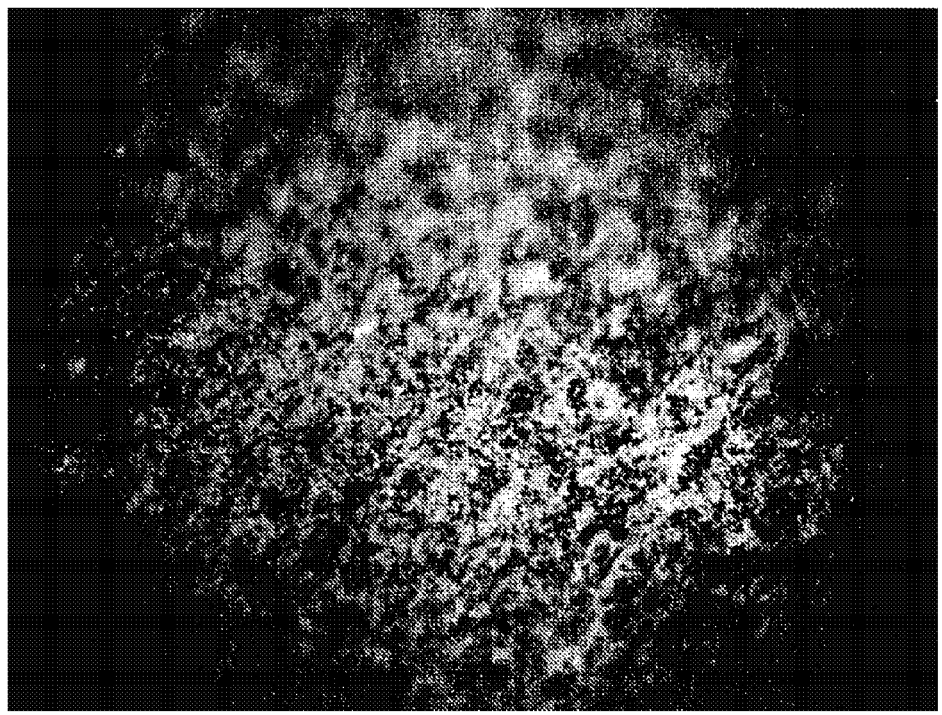
FIG. 1 shows a light microscope image of an enamel and dentin area before and after the fifth exchange. The dentin tubuli are fully closed and a certain brightening is already apparent.

B is preferably a preformulated 50-1000 µm thick gel film.

C is preferably a preformulated 50 µm to 5 mm thick gel film.

0.05 to 3 mol per liter of gel calcium ions $Ca^{2+}$ are preferably contained in C2.

0.01-2 mol per liter of gel of a phosphate or hydrogen phosphate are preferably contained in B2.

The gel former is preferably a common protein hydrolyzate, especially a gelatin.

The gelatin concentration in B and C is preferably 1-15 wt. %, especially 5-10 wt. %.

Phosphate or hydrogen phosphate is preferably present as dissociated $Na_2HPO_4$, $(NH_4)_2HPO_4$, or $K_2HPO_4$.

The calcium ions can be present, for example, as dissociated $CaCl_2$. However, it is also possible to use poorly soluble Ca salts, optionally together with readily soluble ones.

The mineral layer is simultaneously attributed a protective or remineralizing effect with respect to erosion of the dental hard substance, enamel and caries sensitivity. By deliberate reaction and possible incorporation of certain white pigments, the optical properties, with respect to color, brightness and opacity of the firmly adhering mineral layer, can be adjusted.

So as not to threaten the vitality of the tooth and avoid irritation of the gums, the use of concentrated acids or oxidizers is fully avoided.

The kit described here can be used for deliberate, biomimetic mineralization of apatite on tooth surfaces for quality improvement with respect to surface structure. Hypersensitivities related, for example, to porosity of the dental hard substance are considered an appropriate indication for the mineralization-inducing treatment described here. Since layers with a thickness of a few micrometers already cause brightening of the tooth substance, because of the intrinsic color, in certain forms of administration, this method can also be used as a compatible alternative to ordinary bleaching methods, which still have no protective effect on the teeth. The layers are characterized by a distinct gloss, which indicates the limited roughness of the mineral deposit. Mineral loss and the related reduction in gloss by intensive use of abrasive foods can be compensated. The process has nothing in common with neomineralization of already existing nanoscale crystallization nuclei, which is described in patent WO 2005/027863 and is initiated by ions in the saliva. Instead, the effect of layer formation demonstrated in the laboratory is due to direct heterogeneous nucleation of apatite, preferably fluoride-containing apatite, induced by the ions provided in the gel. The dissolved calcium, phosphate and fluoride ions then crystallize from a gelatinous matrix as a firmly adhering layer on the tooth.

As a result of the long action time of the active minerals, highly ordered crystalline layers that are effectively intergrown with the substrate are formed. An optimal effect is observed at an exposure time of the components according to the invention from a day. The minimal exposure time should be more than two hours, preferably more than eight hours. In order to keep the components reliably on the tooth, a covering of water-proof resins or polymers is proposed, for example, a parodontal bandage or a light curing polymer. Polysiloxanes, polyacrylates or polyamides are suitable, for example. The list is inclusive, but not exclusive.

The invention also concerns a method for production of a kit for brightening of teeth with the steps
- 01 Preparation of a solution A according to Claim 1, in which sodium fluoride solution is set at pH 12-14 and mixed with 2-20 wt. % gelatin;
- 02 Preparation of a gel B according to Claim 1, in which 0.1-2 mol/L $NaH_2PO_4$, 0.01-2 mol/L NaF, 0.05-1 mol/L amino acid, 2-10 wt. % acetic acid are dissolved in water,
  the pH value is set with NaOH at 3.5-6,
  the solution is processed to a viscous gel with 10-40 wt. % glycerol and 5-20 wt. % gelatin,
  200-400 μm thick gel films are spread from the still liquid gel, dried and cut to matching pieces or strips,
- 03 Preparation of gel C according to Claim 1, in which a 0.5 to 3 M calcium chloride solution is prepared,
  the pH value is set at 3.5-6.0 with NaOH,
  the solution is processed to a viscous gel with 10-40 wt. % glycerol and 5-20 wt. % gelatin,
  200-400 μm gel films are spread from the still liquid gel, dried and cut into matching pieces or strips.

The invention also concerns a method for cosmetic brightening of teeth, in which
- the tooth surface is pretreated with a solution A according to Claim 1 or a solution A according to Claim 1 is applied and massaged in,
- gel B, according to Claim 1, is applied to the tooth surface,
- gel C, according to Claim 1, is applied to gel B,
- an action time of 1-10 hours is ensured.

Surprisingly, the layers acquire their brightening effect, especially when the ion capacity of the gels is increased and the application amount reduced. In order to store a higher concentration of calcium and phosphate ions in soluble form in the gel, one or more amino acids is preferably added to the gelatin. The amino acids, through their bonding interaction with the mineral salts, act as a depot and optimize their availability. It is assumed that during local depletion of calcium and phosphate as a result of mineralization, the amino acids release ions by shifting the equilibrium. In principle, all amino acids are suitable for bonding calcium and phosphate ions, since, as an amphoteric molecule, they each have an acid and a basic side group. The optimal effectiveness is pH-dependent. This also applies for their buffer property, which can have a stabilizing effect on the pH trend during mineralization. In the immediate vicinity of the mineralization front, these amino acids, having acid groups and releasing calcium, are particularly active as a result of their acid-liberating apatite formation. The availability of phosphate in gel A can preferably be increased by adding amino acids with additional basic groups. To increase the solubility, all substances that have bonding sites for calcium and phosphate ions without precipitating them or having a toxic effect on the human body are suitable. These include vitamins (for example, ascorbic acid), oligopeptides, carboxylic acids, and especially fruit acids, like malic acid, citric acid or pyruvic acid, or sequestering agents, like EDTA. According to the invention, it is proposed to combine one to three different gel layers, in which the sequence is established. If mineral deposition is to occur with only one gel, a calcium phosphate solution is used as a liquid component, which is stabilized by incorporation in the gelatinous medium. Heterogeneous nucleation is initiated by the pretreatment medium. This contains any types of ions that are present in the calcium phosphate solution in a deficit relative to the stoichiometric ratio of apatite. Both a phosphate and calcium or fluoride can then be involved. An induction effect is also achieved by a pH gradient between the pretreatment medium and the gel layer. As an alternative, a two-gel layer method is proposed, in which the cover gel also has an inducing effect on mineralization. The use of thin, preformulated gel films compensates the drawbacks described in US20005220724, which result from the use of a gel applied warm. The thickness of the phosphate gel B or calcium phosphate gel B* is 50-1000 μm, especially 150-500 μm. The concentration of phosphate salts is between 0.01-2 mol/L of gel, preferably 0.08-0.3 mol. The fluoride concentration is 0-0.3 mol/L, preferably 0-0.05 mol/L. In the case of gel B*, the calcium concentration is 0.0001-0.1 mol. The thickness of calcium gel C is between 50 μm and 5 mm, preferably 300 to 600 μm.

DE1020040545847 describes that prewetting of the teeth with 0.05-1 N NaOH has an effect on morphology and growth rate of the layers, especially if calcium ions are added to the solution. It was surprisingly found that a calcium-free alkaline fluoride solution also has a growth-accelerated effect. The concentration of sodium fluoride lies between 0.01-1 mol/L. A damaging effect from unduly high fluoride doses on the body is not expected, since the amounts of employed fluoride solution per tooth lie between 0.02-0.2 mL. Gelatins can be added to the solution, in order to impart a gel-like consistency to them and to improve adhesion on the surface. 1-15 wt. %, especially 5-10 wt. %, are preferably used. The pH value of the solution lies between 8 and 14. Because of this, very thin films are reproducibly formed on the tooth surface, which particularly favor initial mineralization. Depending on the ion content of gel B or B* and C, the pretreatment solution can contain 0.5-3 mol/L calcium or 0-1 mol/L phosphate and/or 0-1 mol/L fluoride.

ADVANTAGES OF THE INVENTION a) It was surprisingly found that the layers, under certain conditions, have high gloss. It is assumed from this that by spreading of thin films, the order of the polypeptide chains in the gelatin-gel is significantly increased relative to dripping of a warm solution and better preorientation is therefore present. As a result, the orientation of the mineralizate is also higher.

b) It was surprisingly found that already after four to six exchange cycles, a distinct brightening of the tooth samples was observed. The brightening effect is intensified with increasing number of exchange cycles. By introduction of appropriate pigments in one or more of the components A, B and C (for example, $TiO_2$, $BaSO_4$, etc.), the brightening effect can also be influenced.

c) In the context of the invention, deliberate biomimetic mineralization of apatite on tooth surfaces is proposed as an alternative, free of side effects, to oxidative bleaching methods. The described treatment can also be used, in order to help teeth that have become dull to acquire new gloss. The reduction in surface roughness connected with this and the high fluoride content in the layers increase the caries resistance of the teeth.

The following examples serve to further explain the invention. Parts and percentages, unless otherwise stated, refer to weight.

EXAMPLE 1

Human tooth material is sawed into four disks with a thickness of two millimeters each and polished to high gloss, in order to obtain the flattest possible surface. One disk consists exclusively of enamel on the surface, one exclusively of dentin and two disks contain both types of hard tissues. Two disks are treated for 10 seconds with 25% phosphoric acid, in order to expose the dentin tubuli, and then washed intensely with running water. The other disks remain unchanged. For alkaline pretreatment, a 0.5 M sodium fluoride solution is set at pH 14 and mixed with 7.5 wt. % gelatin. The tooth disks are coated with this solution and the moisture is then blown off after 60 seconds.

Figure 1B:
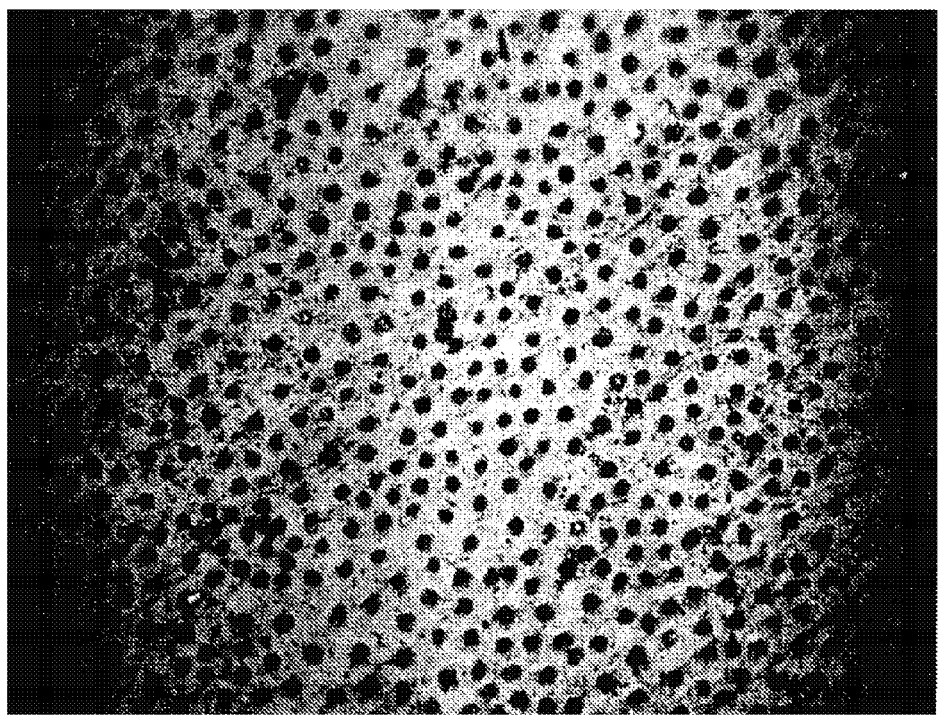

For the phosphate ion-containing gel, a solution is prepared that contains 0.6 mol/L $NaH_2PO_4$, 0.1 mol/L NaF, 0.3 mol/l asparagine and 270 mL 2 N acetic acid. The pH is set at 5.0 with 2 N NaOH. 16 mL of the solution is processed to a viscous gel with 6 g glycerol and 10 g of a 300 bloom pork rind gelatin during heating. By means of a doctor blade, 300 µm thick gel films are spread from the still liquid gel, dried and then cut into matching pieces. For the calcium gel, a 1 M calcium chloride solution is used. Further processing corresponds to that of the phosphate gel. Several tooth disks are now covered, each with a piece of phosphate gel and a piece of calcium gel. In order to make the morphological change of the tooth surface distinct, a disk was half-covered beforehand, so that only half could remineralize. The samples are stored in a climate-controlled cabinet at 37° C. and 95% humidity, washed daily and subjected to repeated gel treatment. After a few exchange cycles, all samples show a uniform coating of biomimetic material, independently of previous etching. FIG. 1 shows a light microscope image of an etched dentin area before and after the fifth exchange. The dentin tubuli are fully closed.

In order to demonstrate the brightening effect, five coated tooth disks were measured, after five-fold gel exchange, with the two-channel spectrophotometer Spectraflash 600 Plus with the CIE L*a*b* System with a 3 mm X4SAV diaphragm. If the enamel area was sufficient, both dentin and enamel measurements were conducted. The following average values from three individual measurements each were obtained for the brightening ΔL:

TABLE 1

ΔL values for dentin and the enamel samples after five-fold gel exchange. The average value for enamel at 2.4 (±1) and at 3.5 (±0.9) for dentin.

|  | ΔL |
| --- | --- |
| P1 dentin (etched) | 4.54 |
| P2 enamel (etched) | 2.41 |
| P2 dentin (etched) | 1.99 |
| P3 enamel (polished) | 1.61 |
| P4 dentin (polished) | 3.9 |
| P4 enamel (polished) | 3.22 |

The measurement, by means of the L-value, shows a distinct increase in brightness, especially on the dentin.

EXAMPLE 2

A front tooth is prepared, so that a smooth enamel surface is exposed, which is polished. The sample is wetted with a 7.5 wt. % gelatin solution, whose pH value lies at 14. 0.5 mol/L sodium fluoride was added to the gel. 50 µL of the solution was massaged onto the tooth surface. Application of the gel films corresponds to example 1.

Figure 2A:
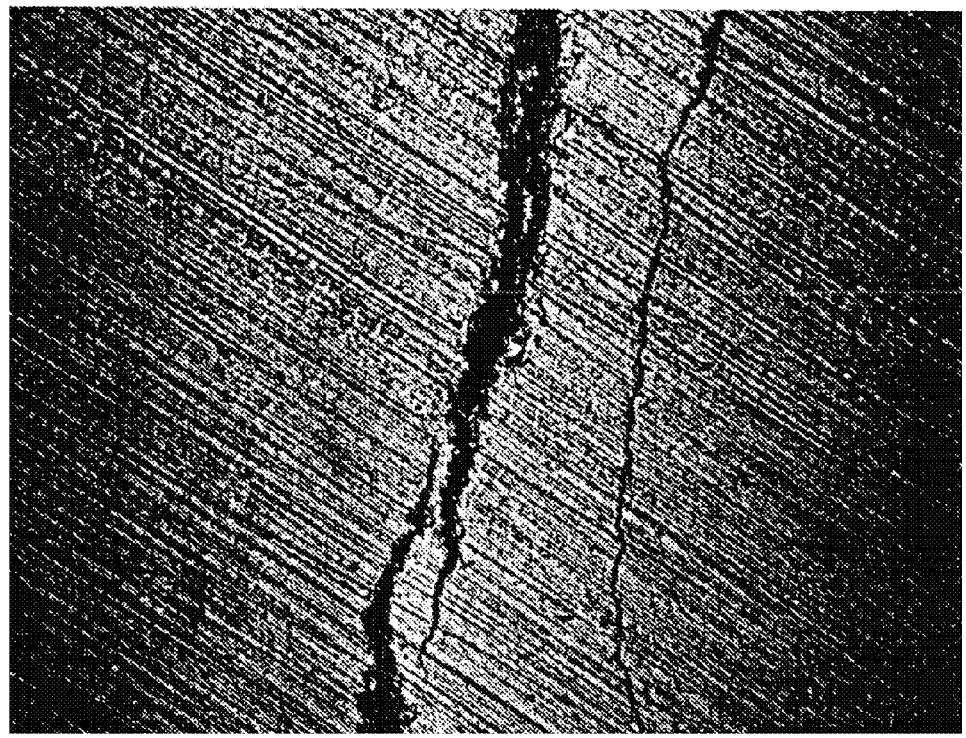
FIG. 2 shows a polished but cracked surface of the enamel area of an incisor before and after the third exchange.
Figure 2B:
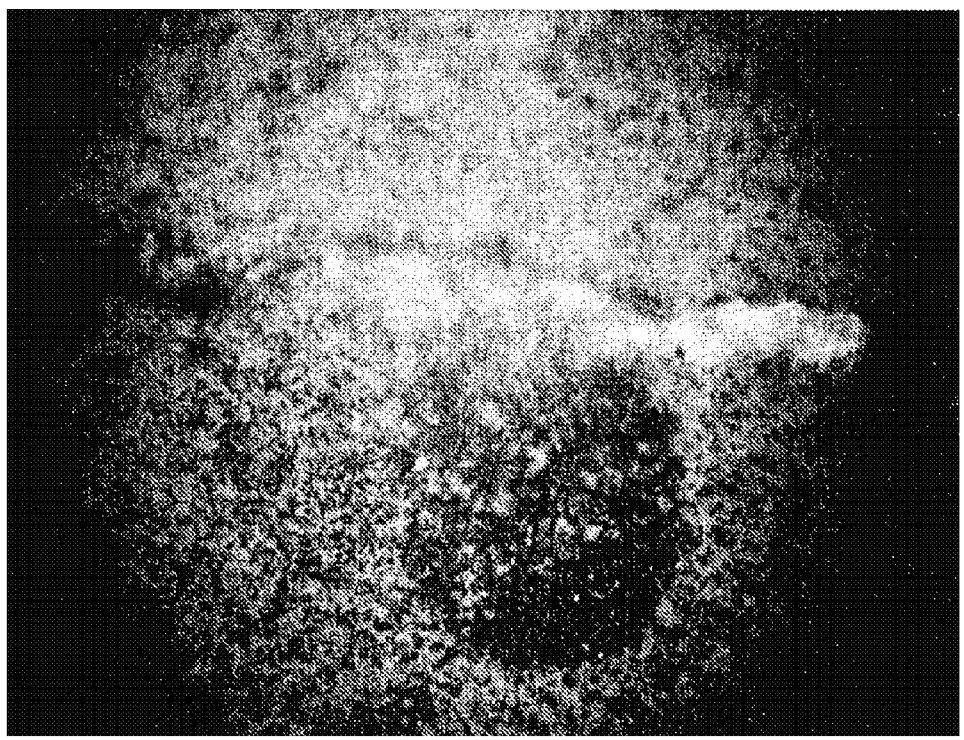

FIG. 2 shows a polished but cracked surface in the enamel area of a front tooth before and after the third exchange. The cracks are scarcely visible and the tooth surface is uniformly overgrown.

What is claimed is:

1. Kit for brightening of teeth, consisting essentially of the following separate components A, B and C:
    A an alkaline, aqueous sodium fluoride solution, optionally comprising a gel former,
    B a dried gel, present in film strips, comprising:
        B1 at least one gel former,
        B2 phosphate or hydrogen phosphate ions,
        B3 optionally at least one amino acid,
        B4 optionally fluoride,
        B5 optionally glycerol,
        B6 optionally carboxylic acid or a buffer system for a pH value from 4 to 7,
    C a dried gel, present in film strips, comprising:
        C1 at least one gel former,
        C2 calcium ions,
        C3 optionally glycerol.
2. Kit according to claim 1, in which
    B is a 50 to 1000 µm thick gel film.
3. Kit according to claim 1, in which
    C is a 50 µm to 5 mm thick gel film.
4. Kit according to claim 1, in which
    0.05 to 3 mol of calcium ions, $Ca^{2+}$, per liter of gel, as measured prior to drying of the film, are contained in C.
5. Kit according to claim 1, in which
    0.01-2 mol of phosphate or hydrogen phosphate ions per liter of gel, as measured prior to drying of the film, are contained in B.
6. Kit according to claim 1, in which the gel former is gelatin.
7. Kit according to claim 6, in which the gelatin concentration in B and C is 1-15 wt. % each.
8. Kit according to claim 7, in which the gelatin concentration is 5-10 wt. %.
9. Kit according to claim 1, in which the phosphate or hydrogen phosphate ions are present as dissociated $Na_2HPO_4$, $(NH_4)_2HPO_4$ or $K_2HPO_4$.
10. Kit according to claim 1, in which the calcium ions are present as dissociated $CaCl_2$.
11. Method for preparation of a kit for brightening of teeth, comprising the steps:
    01 Preparing a solution A according to claim 1, in which the sodium fluoride solution is set at pH 12-14 and optionally mixed with 2-20 wt. % gelatin;
    02 Preparing a gel B according to claim 1, in which
        0.1-2 mol/L $NaH_2PO_4$, 0.01-2 mol/L NaF, 0.05-1 mol/L amino acid, and 2-10 wt. % acetic acid are dissolved in water,
        the pH value is set with NaOH at 3.5-6,
        the solution is processed to a viscous gel with 10-40 wt. % glycerol and 5-20 wt. % gelatin, 200-400 µm thick gel films are spread from the still liquid gel, dried and cut into matching pieces or strips, 03 Preparing gel C according to claim 1, in which
a 0.5 to 3 M calcium chloride solution is prepared,
the pH value is set at 3.5-6.0 with NaOH,
the solution is processed to a viscous gel with 10-40 wt. % glycerol and 5-20 wt. % gelatin,
200-400 µm thick gel films are spread from the still liquid gel, dried and cut into matching pieces or strips.

12. Method for cosmetic brightening of teeth, comprising:
providing a kit according to claim 1,
pretreating a tooth surface with solution A or applying and massaging in solution A,
applying gel B, according to claim 1, to a tooth surface,
applying gel C, according to claim 1, to gel B,
wherein an action time is two to ten hours.

* * * * *